(12) United States Patent
Rigney

(10) Patent No.: US 7,400,981 B1
(45) Date of Patent: Jul. 15, 2008

(54) SYSTEMS, METHODS, AND COMPUTER PROGRAM PRODUCT FOR ANALYZING MICROARRAY DATA

(76) Inventor: David Roth Rigney, 2004#B Ann Arbor Ave., Austin, TX (US) 78704

( * ) Notice: Subject to any disclaimer, the term of this patent is extended or adjusted under 35 U.S.C. 154(b) by 601 days.

(21) Appl. No.: 11/031,390

(22) Filed: Jan. 7, 2005

Related U.S. Application Data

(62) Division of application No. 09/934,156, filed on Aug. 21, 2001, now Pat. No. 7,289,911.

(60) Provisional application No. 60/227,421, filed on Aug. 23, 2000.

(51) Int. Cl.
  *G06F 19/00* (2006.01)
  *G06F 17/50* (2006.01)
  *G01N 33/48* (2006.01)
  *G01N 33/50* (2006.01)
  *G11B 5/02* (2006.01)
(52) U.S. Cl. .............................. 702/19; 703/1; 360/18
(58) Field of Classification Search ....................... None
  See application file for complete search history.

(56) References Cited

U.S. PATENT DOCUMENTS

| | | | |
|---|---|---|---|
| 6,245,517 B1 | 6/2001 | Chen et al. | |
| 6,263,287 B1 | 7/2001 | Zheng et al. | |

OTHER PUBLICATIONS

Andrade et al., Bioinformatics, vol. 15, pp. 391-412, 1999.*
McCallum, www-2.cs.cmu.edu/~mccallum/bow/rainbow, pp. 1-11, 1998.*
Benson et al., Nucleic Acids Research, vol. 25, pp. 1-6, 1997.*
Bairoch et al., Nucleic Acids Research, vol. 25, pp. 217-221, 1997.*
Duggan, D.J., M. Bittner, Y. Chen, P. Meltzer and J.M. Trent, Expression profiling using cDNA arrays. Nature Genetics 21, Suppl 1: 10-14 (1999).
Newton, M.A., et al. On differential variability of expression ratios. Tech. Rept. 139, Dept. of Biostatististics. http://www.stat.wisc.edu/~newton/papers/publications (1999).
Iyer, V.R., M.B. Eisen, D.T. Ross, G. Schuler, T. Moore, et al. The transcriptional program in the response of human fibroblasts to serum. Science 283: 83-87 (1999).
Eisen, M.B, P.T. Spellman, P.O. Brown and D. Botstein. Cluster analysis and display of genome-wide expression patterns. Proc Natl Acad Sci USA 95: 14863-14868 (1998).
Tavazoie, S., J.D. Hughes, M.J. Campbell, R.J., Cho, and J.M. Church. Systematic determination of genetic network architecture. Nature Genetics 22:281-285 (1999).
Tamayo, P. D. Slonim, J. Mesirov, Q. Zhu, S. Kitareewan, et al. Interpreting patterns of gene expression with self-organizing maps. Proc Natl Acad Sci USA 96: 2907-2912 (1999).
Ben-Dor, A., R. Shamir and Z. Yakhini. Clustering gene expression patterns. J. Computational Biology 6:261-297 (1999).

Getz, G., E. Levine, E. Domany, and M.Q. Zhang, Super-paramagnetic clustering of yeast gene expression profiles. arXiv:physics/9911038 at preprint server xxx.lanl.gov (1999).
Perou, C.M., S.S. Jeffrey, et al. Distinctive gene expression patterns in human mammary epithelial cells and breast cancers. Proc. Natl Acad Sci USA 96: 9212-9217 (1999).
Tibshirani, R., et al. Clustering methods for the analysis of DNA microarray data. Manuscript from Web site http://www.stat.stanford.edu/~tibs/lab/publications.html (1999).
Kaufman, L. and P.J. Rousseeuw. Finding Groups in Data: An Introduction to Cluster Analysis. New York: Wiley (1990).
Yeung, K.Y., D.R. Haynor and W.L.Ruzzo. Validating clustering for gene expression data. Manuscript from Web site http://www.cs.washington.edu/homes/kayes/research.html (2000).
Shatkay, H., et al. Genes, themes, and microarrays. Proc. Eighth Inter. Conf. on Intelligent Systems for Molecular Biology, AAAI Press, Menlo Park CA, pp. 317-328. (2000).
Chaussabel, D. and A. Sher. Mining microarray expression data by literature profiling. Genome Biology 2002, 3(10):research0055.1-0055.16 (2002).
Andrade, M.A. and A. Valencia. Automatic extraction of keywords from scientific text: application to the knowledge domain of protein families. Bioinformatics 14:600-607 (1998).
Masys, D.R., J.B. Welsh, J.L. Fink, M. Gribskov, I. Klacansky, & J. Corbell. Use of keyword hierarchies to Interpret gene expression patterns. Bioinformatics 17:319-326 (2001).
Mitchell, T. Machine Learning. New York: McGraw-Hill (1997).
Manning, C.D. and H. Schutze. Foundations of Statistical Natural Language Processing. Cambridge MA: The MIT Press (1999).
McCallum, A.K. Rainbow. Web page from http://www.cs.cmu.edu/~mccallum/bow (1998).
Egghe, L. and R. Rousseau. Introduction to Informetrics. Amsterdam: Elsevier Science Publishers (1990).
Delorie, D.J. Guide: What is DJGPP? Web page from http://www.delorie.com/djgpp/doc/ug/intro/what-is-djgpp.html (1997).
Press, W.H., S.A. Teukolsky, W.T. Vetterling, and B.P. Flannery. Numerical Recipes in C. The Art of Scientific Computing, Second Edn. New York:Cambridge University Press(1992).

\* cited by examiner

*Primary Examiner*—Michael Borin
*Assistant Examiner*—Jason M Sims

(57) ABSTRACT

The present invention relates to systems, methods, and computer program products for the analysis of gene expression data, especially data that have been acquired using microarray technologies. In particular, the present invention relates to methods for analyzing a set of genes that have been partitioned into disjoint subsets known as clusters. It describes methods for quantitatively evaluating the quality of gene clustering, based on the extent to which the similarity of documents associated with genes in a cluster collectively distinguish that cluster from all the other clusters, as well as the extent to which words and phrases, present in documents associated with genes in the cluster, collectively distinguish that cluster from all the other clusters.

2 Claims, 4 Drawing Sheets

SYSTEMS, METHODS, AND COMPUTER PROGRAM PRODUCT FOR ANALYZING MICROARRAY DATA

CROSS REFERENCE TO RELATED APPLICATIONS

This is a division of Ser. No. 09/934,156, filed Aug. 21, 2001 now U.S. Pat. No. 7,289,911. This patent application claims the benefit of U.S. Provisional Application No. 60/227,421, filed Aug. 23, 2000, which is hereby incorporated by reference.

STATEMENT REGARDING FEDERALLY SPONSORED RESEARCH AND DEVELOPMENT

Not applicable.

REFERENCE TO SEQUENCE LISTING, A TABLE, OR A COMPUTER PROGRAM LISTING APPENDIX

A computer program listing, entitled "bow-19991122", was submitted as a compact disc appendix to the related application: Ser. No. 09/934,156, which is cross-referenced above. The computer program listing is hereby incorporated by reference. The bow-19991122 software code is freely available, public domain software, as follows:

It is released under the Library GNU Public License (LGPL). You are welcome to use the code under the terms of the license for research or commercial purposes, however please acknowledge its use with a citation:

McCallum, Andrew Kachites. "Bow: A toolkit for statistical language modeling, text retrieval, classification and clustering."

http://www.cs.cmu.edu/~mccallum/bow. 1996.

BACKGROUND

1. Field of the Invention

The present invention relates generally to the field of bioinformatics, and specifically to systems, methods, and computer program products that make use of clustering of data, statistical natural language processing, and machine learning, for purposes of analyzing data acquired using DNA arrays that have been hybridized with cDNA probes.

2. Description of Prior Art

Disease processes, as well as physiological responses to agents such as drugs and radiation, are often investigated by measuring the amounts of different messenger RNA (mRNA) species in a tissue specimen or in a cultured cell population. The present invention is concerned with analyzing such data, in particular, data acquired through use of a recently developed tool known as microarrays [DUGGAN et al., Nature Genetics 21, Suppl. 1:10-14 (1999)].

Microarrays consist of hundreds or thousands of spots of different DNA sequences, corresponding to many different genes, arranged in a grid pattern on a glass substrate or nylon membrane. Complementary DNA (cDNA) prepared from the mRNA of a tissue specimen is hybridized to the microarray, which is then detected by fluorescence or autoradiographic methods. The signal detected at each of the many spots on the microarray is then used as an indication of the relative amount of the corresponding mRNA species in the specimen.

Microarray experiments are often performed to compare mRNA levels from tissues under two conditions (e.g., cancerous vs. normal cells; before vs. after administration of a drug), in which case, the ratio of estimated mRNA levels for each microarray spot under the two conditions is also ordinarily calculated. The construction or interpretation of such ratio estimates may benefit from the application of statistical corrections, especially when spot values are close to the threshold of measurement detectability [CHEN et al., patent U.S. Pat. No. 6,245,517 (2001); NEWTON et al. (1999) from the Web site having the following domain name—top level domain=edu, second level domain=wisc, third level domain=stat, fourth level domain=www, path=/~newton/papers/publications.

Microarrays have also been used to monitor the time course of mRNA levels in a cell population that had been subjected to an intervention, such as a shift in serum concentration in the growth medium, which alters the concentration of hormones and other factors needed for cell growth [IYER et al., Science 283: 83-87 (1999)]. Those microarray measurements are typically made from mRNA collected at short time intervals (on the order of several minutes) immediately after application of the intervention, and longer intervals thereafter (hours). cDNA prepared from each of these mRNA samples is ordinarily hybridized to a separate array. Ratios are then constructed for each time point, as mentioned above, by dividing the measurement at each microarray spot at the time point, by a measurement corresponding to time-zero for that microarray spot. After inspecting the time course of estimated mRNA levels for all the genes on the arrays in those experiments, investigators noted that the mRNA levels for certain groups of genes tend to fluctuate up and down together. Subsequently, computer algorithms were used to group together sets of genes (known as "clusters", produced by a clustering algorithm) according to the similarity of the time-course of their estimated mRNA levels, making the groupings more objective and relieving investigators of the burden of grouping the genes by eye [EISEN et al., Proc. Natl. Acad. Sci. USA 95: 14863-14868 (1998); TAVAZOIE et al., Nature Genetics 22: 281-285 (1999); TAMAYO et al., Proc. Natl. Acad. Sci. USA 96: 2907-2912 (1999); BEN-DOR et al., J. Computational Biol. 6: 281-297 (1999), GETZ et al. (1999), arXiv: physics/9911038 from the Web site having the following domain name—top level domain=gov, second level domain=lanl, third level domain=xxx; ZHENG et al., patent U.S. Pat. No. 6,263,287 (2001)].

Microarrays have also been used to measure cell responses to several different types of interventions, at a single time point, rather than the response to a single intervention at a series of time points. In those experiments, groups of genes were also observed to exhibit similar mRNA levels in response to the various interventions, and groupings of those genes were also produced automatically by using clustering algorithms [PEROU et al., Proc. Natl. Acad. Sci. USA 96: 9212-9217 (1999); TIBSHIRANI et al. (1999) from the Web site having the following domain name—top level domain=edu, second level domain=stanford, third level domain=www-stat, path=/~tibs/lab/publications.html The similarity of estimated mRNA levels—observed among genes in individual clusters—could in some instances be coincidental, but most investigators attribute the similarity of mRNA levels to unknown biological control mechanisms, whereby functionally related genes are transcribed in a coordinated fashion in order to participate stoichiometrically in a biochemical or cell-physiological process. Thus, the clustering of genes on the basis of the similarity of their mRNA levels is viewed by investigators as an initial step in identifying functionally significant biochemical pathways or cell-physiological processes and their mechanisms of transcriptional control. For example, genes involved in mediating progression through the cell cycle may be found in the same cluster [IYER et al., supra]. However, it has also been observed that genes with supposedly similar known functions do not always appear together in the same clusters [TAVAZOIE et al., supra]. This may be due in part to inadequacy of the particular clustering algorithm that was used. If a different clustering algorithm were applied to the data, it would generally produce different clusters and may be more successful at grouping together functionally related genes.

Initially, investigators applied hierarchical clustering algorithms to array data [EISEN et al. supra]. Later investigators used self-organizing maps to perform clustering [TAMAYO et al., supra]. Other investigators have performed clustering of microarray data using the k-means algorithm [TAVAZOIE et al., supra], a graph theoretical algorithm [BEN-DOR et al., supra], super-parametric clustering [GETZ et al., supra], as well as grid and σ-τ clustering [ZHENG et al., supra]. Variations of these algorithms have also been implemented by using various normalizations and distance measures. Additional clustering algorithms were described for situations in which data are parameterized by two or more variables [TIBSHIRANI et al., supra]. Considering that hundreds of other general-purpose clustering algorithms have been described [KAUFMAN and ROUSSEEUW, Finding Groups in Data: An Introduction to Cluster Analysis, Wiley (1990) and references contained therein], many of which may eventually be applied to microarray data, and considering that all of these clustering algorithms may group microarray data in different ways, investigators have the problem of deciding which of those algorithms is most useful for analyzing their data.

One therefore needs to compare results made with different clustering algorithms, in order to decide which algorithm is most useful for the data under investigation. The comparison may be made first in terms of the statistics of how well members of each cluster resemble their corresponding centroid (i.e., tightness of clustering), or in terms of a figure-of-merit obtained using a resampling approach YEUNG et al. (2000) from the Web site having the following domain name—top level domain=edu, second level domain=washington, third level domain=cs, fourth level domain=www, path=/homes/kayee/research.html. However, such goodness-of-fit comparisons do not assess the quality of clustering in terms of the biological reasonableness of the results, which must be based on the physiological functions of the genes in the clusters.

However, there is little prior art that can assist investigators in evaluating the extent to which genes in clusters are functionally related, which has been taken to be a primary criterion upon which the quality of clustering is judged. The main difficulty in establishing functional relations among genes in clusters lies in the unavailability or incompleteness of factual databases that explicitly link the known functions of genes with one another. TAVAZOIE et al., supra, indexed yeast genes using the 199 functional categories in the Martinsreid Institute of Sciences functional classification scheme database (ribosomal, mitochondrial, TCA pathway, etc.). For each cluster of genes, they then calculated probabilities (P values) of the frequency of observed genes in the various functional categories, to determine whether particular clusters are significantly composed of genes associated with particular functional categories. However, such functional classification databases are available to characterize the genes of only a limited number of organisms, or they may not contain a complete list of known genes. Furthermore, those databases force genes into a predetermined classification scheme that may contain overly-broad or overly-narrow classifications, or classifications that are not mutually exclusive. Possibly for this reason, TAVAZOIE et al., supra, found that genes with supposedly similar known functions—as defined by the Martinsreid Institute of Sciences functional classification scheme database for yeast—do not preferentially appear together in the same microarray cluster.

Consequently, many investigators simply review the lists of clustered genes manually and then offer expert commentary about the functional significance of genes in the various clusters, based on their reading of the literature about those genes. For example, IYER et al., supra, describe one cluster as being enriched for genes "involved in mediating progression through the cell cycle", describe another cluster as containing genes encoding "proteins involved in cellular signaling", and for other clusters they offer no description. At the present state of the art, expert human judgement may well be the best method for evaluating the relatedness of functions of genes in clusters. However, this method is limited by the expertise of its practitioners, as well as by the considerable labor involved in manually reviewing literature concerning the many genes that may be present in the clusters. In fact, even the task of identifying the relevant articles in the scientific literature is arduous.

Therefore, a practical impediment in interpreting microarray data is the time and effort needed to acquire literature about genes represented on microarrays, as well as the time and effort needed to manually review and integrate the information contained within that literature. It is consequently an objective of the present invention to produce automatically generated, quantitative indices (figures-of-merit) of the extent to which genes in a cluster are functionally related to one another, based solely on information within the scientific literature concerning genes present on a microarray. Investigators may use the indices to evaluate the functional relatedness of genes in clusters that were made using a particular clustering algorithm, as well as to compare the performance of different clustering algorithms. In so doing, investigators may use the figure-of-merit indices that are generated by the method to evaluate the quality of different clustering algorithms, based solely on the content of the literature about the genes associated with the clusters. An advantage of the present method and system is that it does not presuppose the existence of a structured database of gene annotations, such as the Martinsreid Institute of Sciences functional classification scheme database for yeast, which was mentioned above.

There is little prior art that that can assist an artisan in automatically generating a useful corpus of literature about an individual gene, which might then be used to analyze the literature about the genes that constitute a microarray cluster. PubMed/MEDLINE is the most widely used on-line source for gene-related abstracts and literature, which might be used to generate such a corpus, but few investigators have described its use for any similar purpose. SHATKAY et al., Internat. Conf. on Intelligent Systems in Molecular Biology 8: 317-323 (2000), explain that PubMed provides for literature search and retrieval by two methods—boolean query and similarity query (also known as "neighboring"). They describe how there are well-known deficiencies with any attempt to use the method of boolean queries to generate a text corpus. For example, CHAUSSABEL and SHER, Genome Biology 3(10):research0055.1-0055.16 (2002) attempted to use boolean queries consisting of gene names taken from a list, and ultimately found it necessary to manually edit or correct the unacceptably large number of errors that resulted from use of boolean queries. Accordingly, SHATKAY et al. advocate using only the neighboring feature of PubMed to acquire a set of documents about a gene, after first selecting a "kernel" citation for that gene, possibly from within a curated database about the genes under investigation. The literature in PubMed that "neighbors" this kernel citation is then generated by PubMed after providing it the kernel citation as the neighboring query. The method of SHATKAY et al. then seeks to find similarities within the documents so generated for different genes. This method can be automatic only if there already exists a curated citation list from which to obtain the "kernel" documents, as was the case with the yeast genes investigated by SHATKAY et al. Otherwise, and in general, an expert human would need to select the kernel documents. Furthermore, SHATKAY et al. teach that when a clustering of genes is already available from microarray expression experiments, then that clustering should be ignored, except for purposes of manually comparing with results obtained independently by their method. Thus, unlike the present invention, their method does not use the actual clustering of microarray data, and it provides no figure-of-merit for the quality of microarray clustering. Another method for generating a corpus of text using MEDLINE was described by ANDRADE and VALENCIA, Bioinformatics 14: 600-607 (1998), but it was used to generate a text corpus only for protein domain families, rather than for individual, arbitrarily selected genes. In their method, protein families in the PDB-SELECT database pointed to entries in the SwissProt database, which pointed to articles in MEDLINE, which were then taken to be the corpus for the corresponding protein domain family. This method is not generally applicable to the problem of generating a literature corpus for an arbitrarily selected gene, because a gene may not belong to a known protein family. Furthermore, the size of the literature corpus generated by their method would be limited by the number of pointers in the SwissProt database. Unlike the present invention, their method does not make use of information from the clustering of microarray data, and it provides no figure of merit for the quality of microarray clustering.

The present method and system also produces text for each cluster in a different manner than what was described by MASYS et al., Bioinformatics 17: 319-326 (2001). Unlike the present invention, their method does not provide a figure of merit for the quality of microarray clustering. Their method also has the disadvantage that the words and phrases it produces are voluminous and generally non-specific, placing a significant burden of interpretation on the investigator, because it links sets of genes to the published literature by way of keyword hierarchies using the entire set of descriptors contained in MeSH and Enzyme Commission nomenclature.

Given all the above-mentioned limitations of the prior art, it was therefore an aim of the present invention to provide a method for automatically generating a substantial literature text corpus for an arbitrarily selected known gene, which could then be used to generate a text corpus for clusters obtained from microarray experiments, suitable for generating a figure-of-merit index indicating whether each particular microarray clustering has support in the scientific literature.

In one embodiment, the present invention obtains text in the scientific literature about genes on a microarray by following links about each gene in databases of the National Institutes of Health (NIH) to a corresponding entry in the NIH database "Online Mendelian Inheritance in Man" (OMIM). The latter database contains literature citations about the corresponding genes, text from which is downloaded from another NIH literature database and which is used to construct a text corpus for each grouping of genes that constitute a microarray cluster.

The present invention then makes use of concepts of machine learning and statistical natural langnge processing [MITCHELL, Machine Learning, McGraw-Hill (1997); MANNING et al., Foundations of Statistical Natural Language Processing, MIT Press (1999)] by treating the problem of interpreting literature about microarray clusters as one of text categorization, the goal of which is to classify the theme of any particular document. The rationale of the disclosed method is that if the microarray clusters correspond to distinctions that would be meaningful to a biologist reading the literature about genes in the clusters, then such distinctions can be made quantitatively in terms the frequent appearance of words or phrases that are contained within the text corpus for each cluster and simultaneously in terms of the infrequent appearance of such words or phrases with the text corpus for other clusters. To the extent that quantitatively distinguishing words and phrases can be found for each cluster, then we may use them to construct a text classifier that predicts whether a gene is associated with a particular cluster, based on the quantitative word/phrase composition of literature documents about that gene. Conversely, if the microarray clusters do not correspond to distinctions that would be meaningful to a biologist reading the literature about genes in the clusters, then it should not be possible to construct a text classifier that reliably predicts whether a gene is associated with a particular cluster, based on the quantitative word/phrase composition of literature documents about that gene.

The figure-of-merit indices of the present invention relate to the percentage of times that tested classifications are made correctly, as compared with classifications performed on text corresponding to genes placed randomly into clusters. Although the invention makes use of some conventional procedures of supervised machine learning, as implemented in the open source software "rainbow" (described in documentation at the Web site for the "bow" software, top level domain=edu, second level domain=cmu, third level domain=cs, fourth level domain=www, path=/~mccallun/ bow [McCALLUM (1998)]), the invention differs from the existing supervised machine learning art in that the categories into which documents are to be classified are not pre-selected by the artisan to be meaningful, but correspond instead to automatically generated microarray clusters, which may or may not be biologically meaningful entities. In fact, an objective of the invention is conversely to analyze the extent to which the microarray clusters (supervised machine-learning classification categories) are actually biologically meaningful.

In another embodiment of the invention, figure-of-merit indices are calculated by obtaining text in the scientific literature about genes on a microarray; by putting that literature in groups defined by microarray clustering of the corresponding genes; and by then evaluating the extent to which genes within a cluster are associated with the same literature citations, irrespective of the actual text within those literature citations. Indices are then generated by calculating the average fraction of times that pairs of genes in a cluster are associated with the same literature citation. Because the indices are based on literature citations rather than text within the citations, the indices are related to concepts that arise in connection with the analysis of literature co-citation frequencies [EGGHE and ROUSSEAU, Introduction to Informetrics, Elsevier Science Publ. (1990)], but which have nothing to do with the analysis of microarray data.

BRIEF SUMMARY OF THE INVENTION

A system and methods for analyzing microarray data includes a computer having a central processing unit and a computer memory, which are used to run computer program modules. The computer program modules, along with experimental signal data representing relative concentrations of particular mRNA species (indexed as nucleic acid accession numbers), are loaded initially into the computer memory from a computer disk. One computer program module groups the mRNA species (or nucleic acid accession numbers) into clusters, each cluster being a subset of the mRNA species (or of the corresponding nucleic acid accession numbers). Other computer program modules associate multiple unique identifiers, corresponding to scientific publications describing gene structure and functions, with each of the genes in each of the clusters.

In one embodiment of the invention, a computer program module obtains literature abstracts and other text corresponding to the above-mentioned literature unique identifiers. A computer module organizes that text in computer files according to the clustering of the corresponding genes, then constructs a mathematical model of the text. The purpose of the model is to identify words or phrases in the text that are most uniquely associated with the text corresponding to each cluster, and that also best distinguish each cluster from the others. Another computer program module produces a quantitative index of the relatedness of genes within each cluster, by testing the model's ability to classify additional text about genes in the clusters. In this embodiment, a figure-of-merit index, which is generated by the method and system, relates to the percentage of times that the test classifications are made correctly, as compared with classifications performed on text associated with genes that had been clustered randomly.

In another embodiment of the invention, a computer program module calculates an index of the functional relatedness of genes within each cluster, by calculating the average fraction of times that pairs of genes in the cluster are associated with the same literature unique identifier. Another computer program module randomizes the assignment of genes to clusters, then calculates the percentage of times that the index of functional similarity could have occurred by chance.

Output data are accumulated and presented concerning the above-mentioned clusters, words and phrases, as well as the indices of functional relatedness of genes within clusters.

OBJECTS AND ADVANTAGES

Objects and advantages of the present invention include the following:

The prior art provides no methods for obtaining quantitative indices for judging the quality of microarray clustering results, independent of the microarray data themselves, other than those involving databases that have already grouped genes into predetermined functional classes, e.g., the Martinsreid Institute of Sciences functional classification scheme database for yeast. An objective of the present invention is to generate quantitative indices about the functional, structural, or biochemical pathway relatedness of genes in clusters, using literature databases such as PubMed, in which the connections between genes are implicit in the frequency with which literature about different genes uses the same words and terms. An advantage of such quantitative indices is that, in this invention, they can be generated automatically, and their generation does not force genes into a predetermined classification scheme, which may contain overly-broad or overly-narrow classifications. A yet further advantage of the invention is that it provides an automatic method for identifying a relevant literature for purposes of automatic analysis of the quality of clustering. A still further advantage of the invention is that for genes associated with a cluster, it permits a ranking of the importance of the genes on the basis of the relevance of text in literature about the set of genes in a cluster. A further advantage of the invention is that it ranks the relatedness of a cluster to all the other clusters, on the basis of the similarity of text in literature about genes in the clusters.

DETAILED DESCRIPTION OF THE PREFERRED EMBODIMENTS

The present invention is not limited to any particular hardware or operating system environment. Those skilled in the art will understand that the systems and methods may be implemented using a variety of computer platforms, operating systems, and programming languages. Therefore, the following description of specific embodiments of the present invention is for purposes of illustration only.

Hardware

Figure 1:
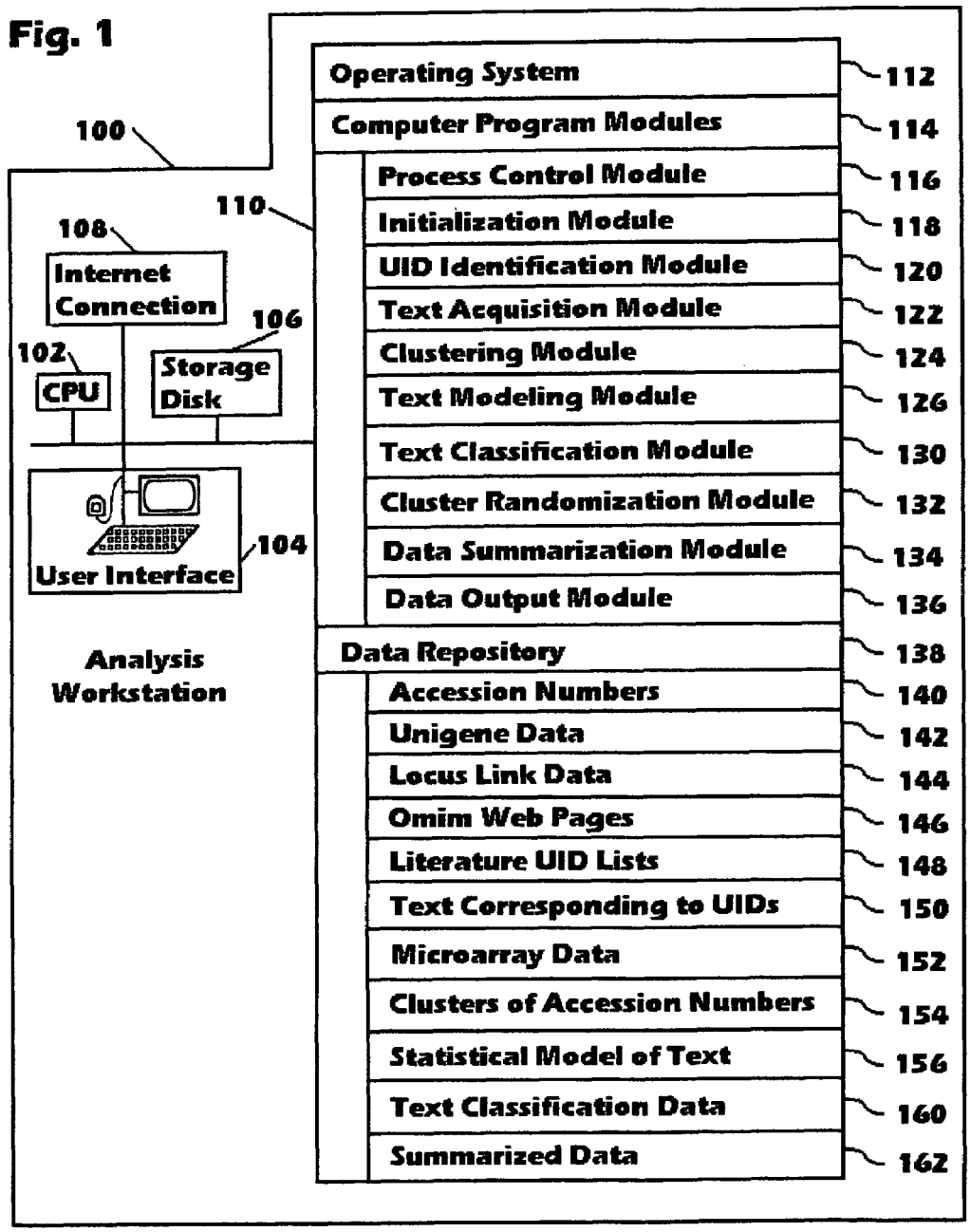
FIG. 1 is a block diagram of a preferred embodiment of the system and computer program product for analyzing microarray data.

The device for analyzing microarray data is shown in FIG. 1. It consists of a computer workstation (100), which has a Pentium III central processor unit, abbreviated as CPU (102), and which is connected to the Internet using a cable modem and a 10/100 network interface card (108). The workstation's User Interface (104) makes use of a monitor, keyboard, and mouse. The workstation's operating system, computer program modules, and data repository are loaded into a 512 Megabyte computer memory (110) from files on a 34 Gigabyte hard storage disk (106).

Operating System

The operating system for the workstation (112) is Microsoft Windows 98, augmented with additional software that allows operation of the workstation to resemble a UNIX system, namely, operate in the GNU software environment, which is described at the Web site having the following domain name—top level domain=org, second level domain=fsf, third level domain=www. This additional software is DJGPP version 2.03 [Delorie (1997)], obtained over the Internet at the ftp site having the following domain name—top level domain=net, second level domain=simtel, third level domain=ftp, path=/pub/simtelnet/gnu/djgpp. The workstation's augmented operating system contains all the utility programs that are customarily downloaded for installation with DJGPP, such as perl, flex, bash, grep, and GNU Fileutils.

Installation of DJGPP is necessary in order to install the text modeling program module (126), and text classification module (130). These modules make use of the "bow" software toolkit for statistical language modeling, text retrieval, classification, and clustering (version 1999.11.22), which was downloaded from the Web site having the following domain name—top level domain=edu, second level domain=cmu, third level domain=cs, fourth level domain=www, path=/~mccallum/bow and which is hereby incorporated by reference, in particular, its open source code. Installation of the "bow" software toolkit was performed as described in the instructions that come with the toolkit, except that the system utility program "autoconf" was run to produce a new "configure" file, instead of using the "configure" file that came with the distributed "bow" software.

Computer Program Product

The computer program modules (114) are loaded from the computer storage disk (106) into the computer memory (110) in order to perform individual tasks in the analysis of microarray data. Because some Users may already have the hardware and operating system software of the system, which are described above, the computer program modules (114) along with the associated data repository (138) by themselves constitute a computer program product, which such Users would then install on their available computers.

Process Control and Specifying Options

The analysis process is initiated by the User at the User Interface (104), for example, by typing the name of the Process Control Module (116) at a DOS prompt, which causes the operating system to load and run the Process Control Module (116). At the time of initiation, the User may also specify analysis options, for example in an "[argv[ ]" command line format that is used for computer programs written in the C Language. The options instruct the Process Control Module to proceed in a manner other than by using default parameters of the analysis process. These options are stored for subsequent use as the values of variables within the Process Control Module.

The Process Control Module, in turn, loads and runs other modules, many of which could actually be run independently by the user. For example, the User could type the following MS-DOS or bash command line to cause a computer program called "rainbow" to perform text classification of text files located in subdirectories of a directory called "clusters_text", and then place the results of the classification in a directory called "text_model" (as described in documentation at the Web site for the "bow" software, [MCCALLUM (1998)], from the Web site having the following domain name—top level domain=edu, second level domain=cmu, third level domain=cs, fourth level domain=www, path=/~mccallum/bow rainbow -d .\text_model—index .\clusters_text\*

However, the Process Control Module (116) does the same thing automatically as one of the steps in the overall analysis process, by running the Text Modeling Module (126) that in turn runs the "rainbow" program The program line within the Text Modeling Module (126) that does so, written in the program language C, is as follows:

system("rainbow -d .\\text_model—index .\\clusters_text\\*");

It is well known by computer programmers that the same type of process control can also be accomplished by using a shell script, or by jumping directly to computer memory locations corresponding to compiled libraries or subroutines, rather than by invoking such a system(" . . . ") function within a compiled computer program.

GLOSSARY

Description of the method used in the workstation system (100) to analyze microarray data follows. In order to assist the reader to understand the description, the following glossary of terms is first provided.

Accession number or gene accession number: A researcher who sequences some DNA often deposits that sequence information into a public DNA sequence database, such as GenBank. When the curators of the DNA sequence database enter that sequence information into the database, they assign a unique, permanent identifier to the sequence, which is known as the sequence's accession number. It consists of an alphanumeric string, such as "W95909". DNA in each spot on the microarray has been sequenced (in whole or in part), and that sequence may be ascertained from a database like GenBank by specifying the known accession number corresponding to that spot.

UniGene Number: Many of the DNA sequences that have been assigned accession numbers are similar to the sequences corresponding to other accession numbers, because different researchers may have sequenced the same gene and deposited the sequence information independently. UniGene is a database that groups together different accession numbers corresponding to similar sequences. Each such grouping of accession numbers is assigned a number (UniGene number). Thus, the accession numbers that have been assigned a particular UniGene number have DNA sequences that are similar to one another.

LocusLink Number: The Locus Link database groups together entries from several databases that involve not only DNA sequence information (such as UniGene data), but also such things as the chromosomal location of the DNA sequence, the Enzyme Commission number of the corresponding protein (if it is an enzyme), and the diseases with which the corresponding gene are associated (if known). Each grouping of database entries about a particular gene is assigned a number (Locus Link number). NOTE: Sponsors of the Locus Link database plan to incorporate it into a larger database known as Entrez Gene, at which time Entrez Gene will replace Locus Link.

Omim Number: Omim is an abbreviation for "Online Mendelian Inheritance in Man", which is a database that describes the connection between particular genes and diseases. Each gene in the Omim database is assigned an identifying number (Omim number). The Locus Link database entries include the Omim number if it exists. There is a Web page for each of the genes in the Omim database, which contains links to relevant scientific literature about the corresponding gene.

UID or PubMed UID: PubMed is a database of biomedical scientific publications. Every scientific article from the journals that are indexed by PubMed is identified by a unique, permanent number—the Unique IDentifier number ("UID" or "uid").

rainbow: This is the name of a computer program written by McCallum and colleagues at Carnegie Mellon University. It may be used to classify text files. Given examples of text files that deal with a specified number of different subjects (classes), it first examines the text in those files to determine the vocabulary that distinguishes the different subjects (classes). Then, given a text file on an unknown subject, it classifies that file as pertaining most closely to one of the different known subjects, based on the vocabulary that it contains.

Process of Analyzing Microarray Data

The Process Control Module (116) begins the analysis by initiating tasks that are to be accomplished by the Initialization Module (118). The first such task is to read a file of gene accession numbers, corresponding to the DNA species that have been spotted onto the microarray under investigation, for which partial sequences are known. The list of accession numbers are stored for future use in the Data Repository (138), in the section Accession Numbers (140).

The next task of the Initialization Module (118) is to associate each of the accession numbers with a gene that has been characterized (if possible). It does so by first converting accession numbers to UniGene numbers. It then converts UniGene numbers to LocusLink numbers. Finally, it converts LocusLink numbers to Omim numbers. Each of these conversions is accomplished by using look-up table data, in which the associations between the labelings of different types of data are listed explicitly. These steps are described in more detail in the paragraphs that follow.

The data pointing from accession numbers to UniGene numbers are read by the Initialization Module (118) from a file on the storage disk (106) and stored in the Data Repository in the section UniGene Data (142). The data in that file are obtained for each new build of UniGene by downloading the file Hs.data.Z (for human genes) from the Web site having the following domain name—top level domain=gov, second level domain=nih, third level domain=nlm, fourth level domain=ncbi, fifth level domain=ftp, path=/pub/schuler/Unigene then extracting the accession-to-unigene number data and formatting the data for storage on the disk (106). The extraction consists of uncompressing the compressed file to become Hs.data, then scanning the resulting text file for lines containing ID Hs."u" followed by SEQUENCE ACC="a", where "u" is a UniGene number and "a" is a corresponding accession number.

The procedure described above pertains to microarray data concerning human DNA. For non-human species (e.g., mouse and rat), the "Hs" in the paragraph above is replaced by the symbol for each of the corresponding species. If the microarray data under analysis are non-human, an additional step is performed to convert the non-human indices to those for the homologous human genes. This extra step consists of using a look-up table to link the UniGene number for the non-human gene with the homologous human UniGene number. The file hmlg.ftp, downloaded from the Web site having the following domain name—top level domain=gov, second level domain=nih, third level domain=nlm, fourth level domain=ncbi, fifth level domain=ftp, path=/pub/Homologene and stored on the workstation's disk (106), contains that look-up table data. It is read by the Initialization Module (118), which stores the data in the UniGene Data section (142) of the Data Repository (138).

The data pointing from UniGene to LocusLink numbers are also read by the Initialization Module (118) from a file on the storage disk (106) and stored in the Data Repository in the section LocusLink Data (144). The data in that file had also been extracted from the file Hs.data. The extraction consists of scanning the text file for lines containing ID Hs."u" followed by LOCUSLINK "L", where "u" is a UniGene number and "L" is the corresponding LocusLink number.

The data pointing from LocusLink to Omim numbers are also read by the Initialization Module (118) from a file on the storage disk (106) and stored in the Data Repository in the section LocusLink Data (144). The data in that file had been extracted from the file LL_templ, downloaded from the Web site having the following domain name—top level domain=gov, second level domain=nih, third level domain=nlm, fourth level domain=ncbi fifth level domain=ftp, path=/refseq/LocusLink. The extraction consists of scanning the text file for lines containing >>"L" followed by OMIM:"o", where "L" is the LocusLink number, and "o" is the corresponding Omim number.

The Initialization Module (118) then links the Accession Numbers in (140) to Omim numbers by following the pointers to UniGene numbers, then to LocusLink numbers, then to Omim numbers. Sometimes, no Omim number can be associated with an accession number because the corresponding pointers do not exist. In that case, the accession number is associated with a number (zero), indicating that no corresponding Omim number could be found. Sometimes, more than one Omim number can be associated with an accession number, for example, because the LocusLink table links a UniGene number with more than one LocusLink number. In that case, all of the corresponding Omim numbers are placed in the table associated with that accession number entry, which is stored in the LocusLink Data section (144) in the Data Repository (138).

Upon completion of these steps by the Initialization Module (118), the Process Control Module (116) initiates operation of the UID identification module (120). Its function is to construct lists of literature Unique IDentifier ("UID" or "uid") numbers, which uniquely identify publications in the scientific literature that describe the genes associated with the accession numbers of the microarray spots. The UID identification module constructs those lists by first downloading Web pages associated with the Omim numbers, those numbers having been obtained as described in the previous paragraph. The UID Identification module (120) then scans the Omim Web pages for UID numbers, creating lists of UIDs that are associated with the microarray spots that had been linked to the Omim numbers. These steps are now described in more detail.

Specifically, for each Omim number stored in the LocusLink Data section (144) of the Data Repository (138), the UID identification module (120) constructs a Web URL address of the form "http://" followed by a domain name of the following form—top level domain=gov, second level domain=nih, third level domain=nlm, fourth level domain=ncbi, fifth level domain=www, path?query=/htbin-post/Omim/dispmim?"Omnimnumber", where "Omimnumber" is one of the Omim numbers mentioned above. The UID identification module (120) then requests this Web page by placing the Web address onto the Internet over the Internet Connection (108) and waits for a reply. It stores the reply on the disk (106) in the section Omim Web Pages (146), saving it as hypertext markup language text with the name "Omimnumber.html".

After downloading all of the Omim Web page files corresponding to the Omim numbers that had been associated with spots on the microarray, the UID Identification module (120) extracts literature Unique IDentifier ("UID") numbers from these Web page files. It does so by scanning lines in each of the files for text of the form "db=form=6&dopt=d&uid=n1, n2, . . . ", where the integers n1, n2, . . . are a sequence of UID numbers separated by commas. The "db=m" indicates that the UID numbers that follow are from the MedLine literature database. Then, the UID Identification module (120) extracts from the strings the numbers n1, n2, . . . , which are separated by commas, which are bounded on the left by "&uid=", and which are bounded on the right by a character other than a comma or numerals 0 to 9. After all such UID numbers have been extracted from the Omim Web page, any repeated UID numbers are eliminated. In this preferred embodiment, this is done by sorting the numbers in ascending order using a standard sorting algorithm [PRESS et al., Numerical Recipes in C, Cambridge Univ. Press (1992)], then examining them sequentially, removing an entry if it has the same value as the one that was examined previously. The sorted, non-duplicate UID numbers are then stored by the UID Identification Module (120), along with their corresponding Omim number in the section Literature UID Lists (148) of the Data Repository (138).

Upon completion of these steps by the UID Identification Module (120), the Process Control Module (116) initiates operation of the Text Acquisition Module (122). Its function is to download over the Internet and filter the text files that are to be used to characterize the microarray data. When acquiring and filtering these data, the Text Acquisition Module (122) stores text data temporarily in the section Text Corresponding to UIDs (150) in the Data Repository (138). For each UID corresponding to each Omim number, obtained from the section Literature UID Lists (148) of the Data Repository (138), the Text Acquisition Module (122) constructs a Web URL address of the form "http://" followed by a domain name of the following form—top level domain=gov, second level domain=nih, third level domain=nlm, fourth level domain=ncbi, fifth level domain=www, path?query=/htbin-post/Entrez/query?db=m&for m=6&dopt=l&html=no&uid=UID, where "UID" is one of the UID numbers. This Web URL address represents a query to obtain the literature citation, abstract, and indexing terms corresponding to the indicated UID number. The requested output format is MEDLARS, with hypertext formatting removed. Since March 2000, the base URL may also be the base URL may also correspond to a Web site having the following domain name—top level domain=gov, second level domain=nih, third level domain=nlm, fourth level domain=ncbi, fifth level domain=www, path=/entrez/utils/qmap.cgi. (See Web address Web address having the following domain name—top level domain=gov, second level domain=nih, third level domain=nlm, fourth level domain=ncbi, fifth level domain=www, path=/entrez/utils/qmap_help.html for alternate ways to construct the URL). The Text Acquisition Module (122) then requests this Web page by placing the Web URL address onto the Internet over the Internet Connection (108) and waits for a reply. It stores the reply on the disk (106), appending it to a text file having the name of the Omim number with which the UID is associated ("Omimnumber.txt"), with a delimiter line (like ">>UID Uidnumber") written to separate successive UID downloads for that Omim number. All such files are stored by default in a specific directory (\Omim).

When all of the text corresponding to all of the UID numbers for all of the Omim numbers has already been downloaded, the User may also specify as an option that the system use those available files for analysis, rather than download them all again. The Text Acquisition Module (122) may then also filter the text files, depending on the options that had been specified by the User at the User Interface (104). The options are to filter out specific categories of text that are contained in the MEDLARS formatted Web pages. The categories of text are delimited in the files by labels such as AB—(for abstract), TI—(for the title of the literature citation), and MH—(for an index term characterizing the subject of the article), any or all of which can be retained as an option. For example, for the option of analyzing only the literature abstracts, the Text Acquisition Module (122) will scan the text files until the delimiter "AB-" is found and copy the subsequent text to another file containing the filtered text, until another delimiter is found. It then stops copying to the second file until another "AB-" is encountered. The latter file has the same name as the original file, plus an extension like ".AB" appended to the file name, indicating that it contains only the "abstract" category of text. Delimiter lines associating the filtered text with their UID numbers may also be retained as an option.

Clustering of Microarray Data

Upon completion of these steps by the Text Acquisition Module (122), the Process Control Module (116) initiates operation of the Clustering Module (124). Its function is to organize the accession numbers (and therefore the associated UniGene numbers, LocusLink numbers, Omim numbers, and UID numbers and associated text files) into separate groups, known as clusters. The clusters are numbered 1, 2, 3, . . . up to some maximum cluster number (Cmax).

If the clustering has already been performed external to the Computer Program Modules (114), the User must have specified at the User Interface (104) the option of using externally clustered data. In that case, the Clustering Module (124) reads the name of the file that contains the clustering data (specified in the option by the User), then reads that file and places the data it contains in the section Clusters of Accession Numbers (154) in the Data Repository (138). That data consists of the number of clusters (Cmax), as well as the accession numbers contained in each of the Cmax clusters. In principle, the same accession number could be found in more than one cluster, but most clustering algorithms place each accession number in only one cluster. In the event that some of the accession numbers in the section Accession Numbers (140) of the Data Repository (138) are not present in any of the Cmax clusters, they are placed in a cluster of previously ungrouped accession numbers, which is defined to be cluster number "zero".

If the microarray data have not already been clustered externally, the Clustering Module (124) performs the clustering itself. The clustering is performed using microarray data that must be provided in a file that had been specified by the User at the User Interface (104). The microarray data are in the form of a spreadsheet table, in which each row corresponds to the respective accession numbers in the Accession Number section (140) of the Data Repository (138), and the columns correspond to different experimental conditions (e.g., response to different interventions, each measured at a single time point; OR response to a single intervention at an initial time, measured at different subsequent times). The entry in each cell of the table is an integrated spot intensity (normalized so that reference spots have the same values for all conditions, and with unwanted background subtracted), measured in fluorescence or radioactivity units, for the microarray spot associated with that row's accession number. Alternatively, the entry in each cell of the table may be a dimensionless ratio, in which the numerator is the integrated spot intensity for that particular condition or time point, and the denominator is the baseline integrated spot intensity (value in the absence of the intervention, or value at time zero). It is also assumed that any other statistical corrections, such as those described by NEWTON et al., supra, have already been applied, so that any errors introduced by the measurement process itself are largely eliminated. After the microarray data are read from the input file, they are stored in the Microarray Data section (152) of the Data Repository (138).

As an option, the User at the User interface (104) may instruct the Clustering Module (124) to add different amounts of noise to the microarray data described in the previous paragraph, in order to evaluate the robustness of the results that are eventually obtained without the addition of noise. The parameter of the option is the coefficient of variation of the statistical distribution that is sampled and added to the integrated spot intensity or ratio corresponding to each spot of the microarray. The statistical distribution is a Gaussian distribution with a mean equal to the given spot intensity and a standard deviation given by the mean times the coefficient of variation. Sampling of the statistical distribution makes use of standard random number generator methods [PRESS et al., supra]. Because the spot intensity is constrained to be a non-negative number, in the event that the spot intensity becomes negative after addition of the random number, it is then set equal to zero.

Clustering of these data by the Clustering Module (124) is performed using algorithms described in the section "Background—Description of Prior Art." The default method is an adaptation of the k-means algorithm, as implemented in the computer program CLARA [KAUFMAN and ROUSSEEUW, supra], source code for which was downloaded from the Web site having the following domain name—top level domain=edu, second level domain=cmu, third level domain=stat, fourth level domain=lib, path=/general/clusfind. When it was included in our system, CLARA was unchanged, except that we made it possible for CLARA to obtain parameter values for its algorithm from the Computer Program Modules (114), rather than by independently prompting the User for parameter values within the CLARA program. Thus, when using this default algorithm for clustering, the User may specify the parameters for the CLARA program as options at the system's User Interface (104), and the Clustering Module (124) subsequently runs the program CLARA using a system(" . . . ") function, as described earlier. In particular, the User may select the number of clusters that are to be constructed (Cmax). After the clustering has been performed, the Clustering Module (124) stores results in the section Clusters of Accession Numbers (154) of the Data Repository (138), namely, the number of clusters (Cmax), as well as the accession numbers contained in each of the Cmax clusters.

Text Modeling and Classification

Upon completion of these steps by the Clustering Module (124), the Process Control Module (116) initiates operation of the Text Modeling Module (126). Its first function is to group the text associated with accession numbers—the text having been obtained with the Text Acquisition module (122)—so as to correspond to the clusters in the Data Repository section Clusters of Accession Numbers (154). It then produces a statistical model of the text that is suitable for text classification. The model contains, for example, the number of times that a term like "mitosis" appears in different documents. To do so, it first creates a directory called \clusters_text, and within this directory it creates subdirectories \0, \1, \2, . . . , Cmax corresponding to each of the clusters. For each of the accession numbers in data section Accession Numbers (140), it then copies files produced by the Text Acquisition Module (122) into the subdirectories, according to the cluster to which that accession number has been assigned by the Clustering Module (124). If an accession number could not be associated with an Omim number, or if that Omim number could not be associated with any UIDs, then the Text Modeling Module (126) proceeds to the next accession number without copying files. The Text Modeling Module (126) then performs the following system function (written in the C programming language):

system("rainbow -d .\\text_model—index .\\clusters_text\\*");

to instruct the computer program 'rainbow' to use the text found in subdirectories of the directory \clusters_text, make a statistical model of the text, then store the results in a directory called \text_model [McCALLUM, supra]. Results are also stored in the Data Repository (138) in the section Statistical Model of Text (156). When making the statistical model, the rainbow program turns the stream of characters in each file into words called "tokens". By default, all sequences of characters are converted to lowercase (e.g., "A" becomes "a") to form the tokens, and any token that is in a stoplist of common words (e.g., "the", "of", "is") is ignored. The model that is then formed constitutes a sparse matrix of the number of times that each of the tokens is found in each of the text files in each of the subdirectories. Many options for the rainbow computer program may also have been specified by the User at the User Interface (104), which are subsequently passed to the rainbow computer program by the Text Modeling Module (126) using a system(" . . . ") function. The possible options are listed in the documentation for the 'rainbow' computer program at the Web site having the following domain name—top level domain=edu, second level domain=cmu, third level domain=cs, fourth level domain=www, path=/~mccallum/bow, as well as its "rainbow—help" on-line documentation, which are included here by reference. Three examples of those options are as follows. (1) Pass the words of the files through a stemmer (e.g., change "experimenting" to "experiment"). (2) Create N-gram tokens (e.g., with a bi-gram, "cell cycle" is used as a token, not just individual words, "cell" and "cycle"). (3) Prune the word list by ignoring words that occur less than some specified number of times in the text files.

Upon completion of these steps, the Process Control Module (116) initiates operation of the Text Classification Module (130). As described in a previous paragraph, files produced by the Text Acquisition Module (122) were copied into subdirectories \0, \1, . . . , \Cmax, depending on the cluster to which the corresponding accession numbers had been assigned by the Clustering Module (124). The Text Classification Module (130) divides the text files in each of these directories into two sets—a training set and a testing set. The Text Classification Module (130) then learns to predict the cluster number of a text file from the words that it contains, based on the statistical distribution of words present in the training set of files, or more precisely, tokens from those files that are present in the Statistical Model of Text (156) that had been generated by the Text Modeling Module (126). That is to say, the Text Classification Module (130) performs supervised machine learning because it knows the cluster number that is associated with each of the training set files (i.e., the subdirectory in which each of the training set files is found). It then tests its ability to predict the cluster number, using the testing set of files as input. For purposes of predicting the cluster number of a test file, the Text Classification Module (130) uses only information from text in that file. It then compares the results of its prediction with the actual cluster number associated with that file. After performing the prediction for all of the files in the testing set, it constructs a confusion matrix. Rows of that matrix (indexed with i) refer to the actual cluster number associated with the test file. Columns of the matrix (indexed with j) refer to the cluster number that was predicted. Elements of the matrix are the number of times that cluster number j was predicted by the classifier, given that the actual cluster number was i. Perfect classification would occur only if the matrix consisted of zeros except along the diagonal.

For detailed analysis of the classification of particular files in the test sets, the number of times that each particular file was correctly classified, and the number of times that it was incorrectly classified, is also recorded. The files with the highest percentage of correct classifications, as determined by sorting the percentages for all files, ranks those files as being the most relevant to the subject matter that is characteristic of the cluster. Consequently, the accession numbers with which those highly ranked files are associated are also ranked as being the most relevant to the subject matter that is characteristic of the cluster.

The Text Classification Module (130) implements these steps using the rainbow program. It does so using a system function in the C programniing language of the form:

system("rainbow -d .\\text_model--test-set=0.4—test=100 | perl confusion_matrix>confusion_matrix.txt");

where the rainbow option -d .\\text_model indicates the directory location of the text statistics file that was created by the Text Modeling Module (126).

where the rainbow option--test-set=0.4 indicates that 40% of the text files in the subdirectories \0, \1, . . . \Cmax are to be used for testing and the remaining 60% are to be used for training the classifier. The files in the test/train split are selected at random.

where the rainbow option--test=100 indicates that the process of selecting the test/train files, followed by classification, is to be performed 100 times.

and where the results are passed to the perl script "confusion_matrix", which writes each of the 100 confusion matrices to a file named confusion_matrix.txt. This script is the same as the perl script "rainbow_stats" in the rainbow source distribution at the Web site having the following domain name—top level domain=edu, second level domain=cmu, third level domain=cs, fourth level domain=www, path=/~mccallum/bow which is incorporated by reference, except that the script "confusion_matrix" does not write as output any information other than the confusion matrix (lines for writing out the other information are deleted from rainbow_stats to make confusion_matrix). The confusion matrix data are also stored in the Text Classification Data section (160) in the Data Repository (138).

The default method that the program 'rainbow' uses for classification is the Naive Bayes method, otherwise known as Evidence Classification or simply the Bayes method. This method, along with applications related to text classification, is explained in Chapter 6 of MITCHELL, supra. The User at the User Interface (106) may also specify as an option that a different method be used by the computer program 'rainbow' to perform the classification, including support vector machines (svm), term frequency-inverse document frequency (tfidf), probabilistic indexing (prind), maximum entropy (maxent), k-nearest neighbors (knn), EM algorithm (em), Dirichilet kernel (dirk), and Active Learning (active). These options are then requested by the Text Modeling Module (126) by issuing a system(" . . . --method=METHOD . . . ")

command for the indicated options to be performed by the 'rainbow' computer program, where METHOD is one of the methods indicated above in parentheses.

Upon completion of these steps by the Text Classification Module (130), the Process Control Module (116) initiates operation of the Cluster Randomization Module (132). The function of this module is to repeat the steps performed by the Text Modeling Module (126) and Text Classification Module (130), except that the accession numbers associated with the clusters are randomized. The objective of this randomization is to ascertain the extent to which the results that had been obtained with the Text Classification Module (130) could have occurred by chance. The number of clusters (Cmax) and the number of accession numbers within each cluster is not changed by the Cluster Randomization Module (132). Instead, this module takes the list of Accession Numbers in the Data Repository (138) and shuffles their order randomly using a random number generator [PRESS et al. supra]. It then replaces the existing accession numbers associated with the clusters, using the shuffled list of accession numbers. The Process Control Module (116) then causes the previous steps performed by the Text Modeling Module (126) and by the Text Classification Module (130) to be repeated. The confusion matrix output for the randomized cluster data are then stored in the Text Classification Data section (160) of the Data Repository (138). The process of randomizing the accession numbers, text modeling, and text classification is then repeated many times (default number=100), the results of which are also stored in the Text Classification Data section (160) of the Data Repository (138). The User at the User Interface (106) may also select the number of randomizations as an option, rather than use the default number.

Upon completion of these steps, the Process Control Module (116) initiates operation of the Data Summarization Module (134). The purpose of this module is to extract a summary of the confusion matrix data present in the Text Classification Data section (160) of the Data Repository (138). Those matrix data give the number of times that each of the test files were correctly classified or were incorrectly classified as another cluster number. The Data Summarization Module (134) first divides the number of correctly classified files for each cluster by the total number classified, giving the fraction of correctly classified files for each of the many (default=100) randomly sanpled test/train splits of the originally clustered data, as well as for each of the trials in which the clusters' accession numbers were randomized. It then sorts those values for the original clustering in ascending order, to provide an estimated statistical distribution for the fraction of correctly classified files, for each of the clusters. It also sorts in ascending order the values obtained from the trials in which the accession numbers were randomized, to provide an estimated control statistical distribution for the fraction of correctly classified files for each cluster. A Kolmogorov-Smirnov statistical test is then applied to these two sets of data for each cluster, to test the null hypothesis that the two data sets are drawn from the same distribution [PRESS et al., supra].

For each cluster, the mean of the statistical distribution for the fraction of correctly classified files is calculated. This is done for the distribution corresponding to the originally assigned accession numbers, as well as for the distribution corresponding to the randomized accession numbers. The difference between the means (original minus randomized) is then calculated as an overall figure-of-merit index for the quality of the clustering.

Similarly, for each cluster i, the mean of the statistical distribution (original minus randomized accession numbers) for the fraction of files incorrectly classified as cluster j is calculated, where i and j range from 1 to Cmax, and where i is not equal to j. These values indicate the closeness of functional relationship between each pair of clusters, as indicated by the literature about the clusters. Thus, if text about cluster i is frequently mis-classified as text about cluster j, this indicates that the genes in clusters i and j have functions in common.

Upon completion of these steps by the Data Summarization Module (134), the Process Control Module (116) initiates operation of the Data Output Module (136). It provides the results of the figure of merit calculations and the Kolrnogorov-Smirnov statistical tests for each of the clusters. Finally, it provides a graphical display of the text classification results, which gives an indication of the extent to which, on average, the text about each gene within a cluster resembles that of other genes within a cluster, as compared with that of genes selected at random from all the clusters. Examples of the format of that graphical display are given in FIG. 3 and FIG. 4.

Description of Alternate Embodiments

Figure 2:
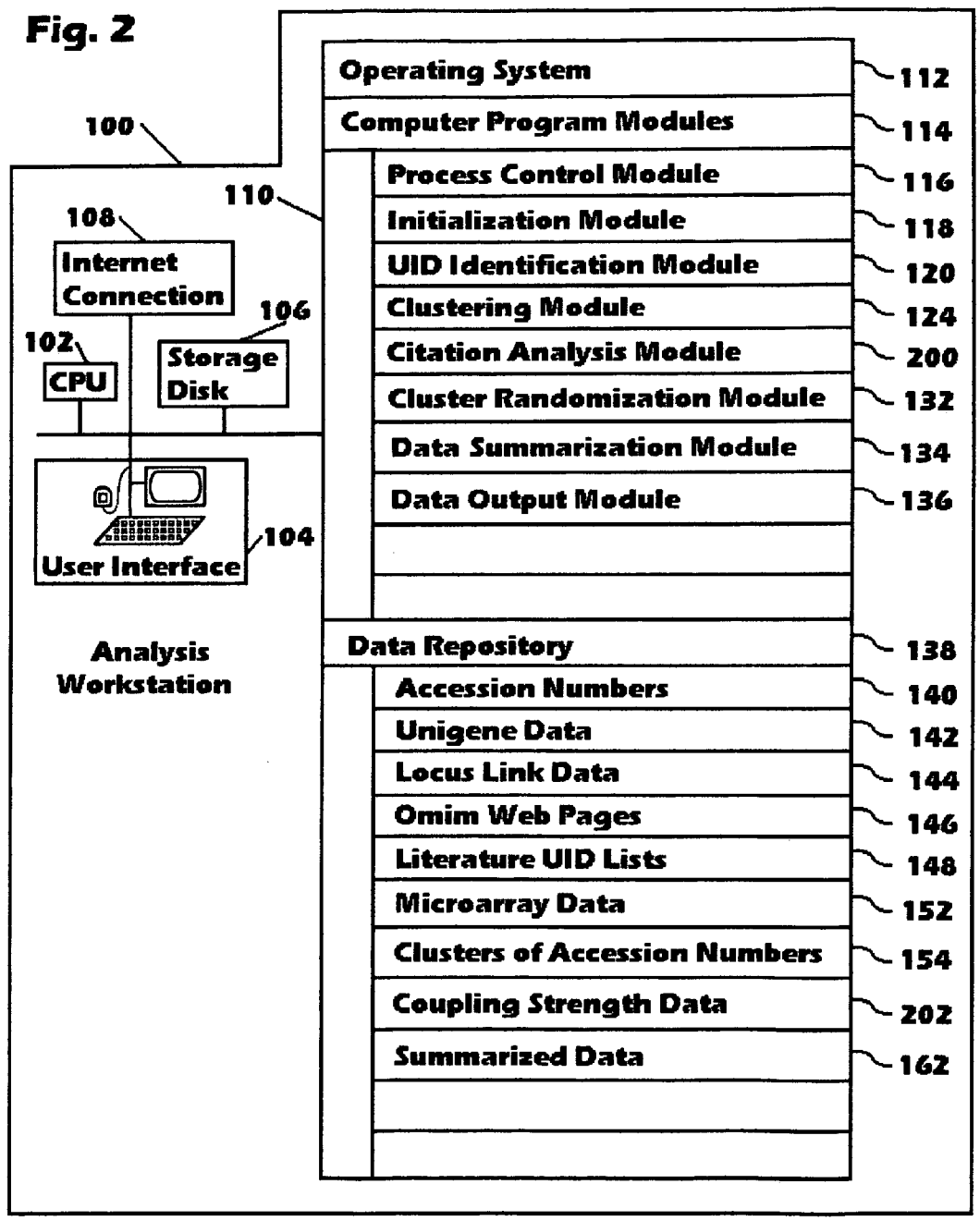
FIG. 2 is a block diagram of an alternate embodiment of the system and computer program product for analyzing microarray data.

The alternate embodiment of the system for analyzing microarray data, shown in FIG. 2, is the same as the preferred embodiment (shown in FIG. 1) except that:
(i) the following computer program modules in FIG. 1 are not used—Text Acquisition Module (122), Text Modeling Module (126), and Text Classification Module (130);
(ii) the following sections of the Data Repositiory in FIG. 1 are not used—Text Corresponding to UIDs (150), Statistical Model of Text (156), and Text Classification Data (160);
(iii) A program module called the Citation Analysis Module (200) and a section of the Data Repository called Coupling Strength Data (202) are found in the alternate embodiment (FIG. 2), but not in the preferred embodiment (FIG. 1).

Operation of the alternate embodiment is the same as the preferred embodiment during the initial steps of the process for analyzing microarray data. The accession numbers are converted to UniGene numbers, which are converted to one or more LocusLink numbers, which are converted to one or more Omim numbers. The system then automatically downloads over the Internet the Web pages associated with the Omim numbers and extracts from them PubMed unique identifiers (uids) associated with those Omim numbers, i.e., a list of publications that can be closely associated with each spot in the microarray. It then removes duplicate uids associated with individual Omim numbers.

For the alternative embodiment shown in FIG. 2, the Process Control Module (116) skips the Text Acquisition Module (122) in FIG. 1 and proceeds to perform the steps of the preferred embodiment for the Clustering Module (124). As with the preferred embodiment, after the clustering has been performed, the Clustering Module (124) stores results in the section Clusters of Accession Numbers (154) of the Data Repository (138), namely, the number of clusters (Cmax), as well as the accession numbers contained in each of the Cmax clusters.

For the alternate embodiment, the Process Control Module (116) then initiates operation of the Citation Analysis Module (200) in FIG. 2. The function of the Citation Analysis Module (200) is to perform a type of 'bibliographic coupling' analysis [EGGHE and ROUSSEAU, supra], in which the coupling strength between 'articles' (Omim Web pages for different genes, where each gene is represented by one Omim Web page) is a function of how many times they cite the same 'paper' (PubMed uid). The method for doing so is now described.

First, the Citation Analysis Module (200) organizes data by creating a directory on the Storage Disk (106) called 'cluster_uids' and places in it Cmax subdirectories corresponding to each of the clusters: \0, \1, . . . \Cmax. In each of the subdirectories it creates a file having the name of each Omim number associated with each of the accession numbers that are associated with the corresponding cluster. The contents of each such file are a list of the uid numbers associated with the corresponding Omim number.

To do so, the Citation Analysis Module (200) combines the following data already present in the Data Repository (138). The Clustering Module (124) had stored the accession numbers corresponding to each cluster in the section Clusters of Accession Numbers (154) of the Data Repository (138). The Initialization Module (118) had linked the Accession Numbers in (140) to Omim numbers by following the pointers to UniGene numbers, then to LocusLink numbers, then to Omim numbers. Furthermore, the sorted, non-duplicate UID numbers were stored by the UID Identification Module (120), along with their corresponding Omim number in the section Literature UID Lists (148) of the Data Repository (138).

Then, for every possible pair of Omim numbers within each of the subdirectories \0, \1, . . . \Cmax, the Citation Analysis Module (200) goes down the list of uid numbers associated with one member of the pair. As it goes, it checks to see whether that uid number is also found in the list of uid numbers associated with the other member of the Omim pair. The total number of matches that it finds is then divided by the total number of uid numbers associated with one or the other Omim number, whichever of the two have the shorter list. This ratio is defined as the 'coupling strength' between the two Omim numbers.

These coupling strength values, which are associated with each possible pair of Omim numbers (within a subdirectory \0, \1, . . . , or \Cmax) are then stored in the section Coupling Strength Data (202) in the Data Repository (138). When all the coupling strengths are calculated for the pairs of Omim numbers in a subdirectory corresponding to a cluster, these coupling strengths are then averaged to provide an average coupling strength for that cluster, which is also stored in the section Coupling Strength Data (202) in the Data Repository (138).

When all the average coupling strength values have been calculated, the Process Control Module (116) passes control to the Cluster Randomization Module (132). It randomizes the assignment of accession numbers to clusters, using the same method that was described in connection with the preferred embodiment. The Process Control Module (116) then passes control back to the Citation Analysis Module (200). The process of calculating an average coupling strength for each of the clusters is then repeated as described above, namely, the association of Omim numbers to the clusters based on their (randomized) accession number composition, the estimation of coupling strength for each pair of Omim numbers in each cluster, and the calculation of an average coupling strength for each cluster. Those results are also stored in the Coupling Strength Data section (202) of the Data Repository (138) for subsequent use. The entire process of accession number randomization and coupling strength calculation is repeated the number of times that was specified as an option by the User (default number of times=100).

The Process Control Module (116) then passes control to the Data Summarization Module (134). For each cluster, the average coupling strengths for the randomized clusters are sorted in ascending order. Then, as an index of the significance of the average coupling strength that had been obtained before randomizing the clusters, the Data Summarization Module (134) determines the percentage of times that the observed coupling strength for each cluster was larger than those obtained with the randomized clusters. For example, if exactly half of the average coupling scores obtained by randomizing the cluster was less than the average coupling score before randomization, the percentage coupling score for that cluster would be 50%. Those percent coupling scores are then stored in the Sununarized Data section (162) of the Data Repository (138) for subsequent display by the Data Output Module (136).

Examples Using the Preferred Embodiments

The examples make use of microarray data that are described in IYER et al., supra, which are available at the Web site having the following domain name—top level domain=edu, second level domain=stanford, third level domain=genome-www. They are from an experiment in which quiescent human diploid fibroblasts were stimulated to proliferate by increasing the concentration of fetal bovine serum in their growth medium. At 12 time points after addition of the serum, samples of mRNA were collected and used to prepare cDNA for hybridizing to an array. Five hundred-seventeen genes on the array were observed to show significant up- or down-regulation, as defined in IYER et al., supra. The microarray data corresponding to these 517 genes were clustered using a hierarchical clustering algorithm [EISEN et al., supra], resulting in 10 clusters, labeled A through J in FIG. 2 of IYER et al., supra. Accession numbers for all the genes represented as spots on the microarray are available at the Web site given above.

Analysis of these data made use of information extracted from Build 96 of the UniGene database, which was contained in the file Hs.data.Z, downloaded from the Web site having the following domain name—top level domain=gov, second level domain=nih, third level domain=nlm, fourth level domain=ncbi, fifth level domain=ftp, path=/pub/schuler/Unigene. The analysis also made use of information extracted from the Locus Link database (version Sep. 10, 1999), which was downloaded as the file LL_templ at the Web site having the following domain name—top level domain=gov, second level domain=nih, third level domain=nlm, fourth level domain=ncbi, fifth level domain=ftp, path=/refseq/LocusLink. Processing of these data to associate the accession numbers with Omim numbers proceeded as described in the Preferred Embodiment, through pointers from accession numbers to UniGene numbers to LocusLink numbers to Omim numbers. Among the 517 accession numbers in the test data, 237 of them could be associated with Omim numbers. Most of the others were unidentified ESTs, which were excluded from further analysis by associating them with Omim number "0".

The UID Identification Module (120) in FIG. 1 then downloaded Omim Web pages corresponding to those Omim numbers and extracted from them Unique IDentifier numbers ("uids"), as described in the Preferred Embodiment. A total of 19,643 uids were associated with 237 Omim numbers.

The Text Acquisition Module (122) in FIG. 1 then downloaded text files corresponding to these 19,643 uids, storing them in 237 files having the names of the corresponding Omim numbers, as described in the Preferred Embodiment.

The Clustering Module (124) in FIG. 1 then clustered the 517 accession numbers using an externally available clustering scheme, which is the one shown in FIG. 2 of IYER et al., supra. The clusters, associated with the accession numbers of the clustered genes, were obtained at the Web site having the following domain name—top level domain=edu, second level domain=stanford, third level domain=genome-www.

For use in the example, the clusters that IYER et al., supra, had labeled A through J were relabeled 1 through 10, and accession numbers that had not been associated with a cluster were put into a cluster "zero".

Figure 3:
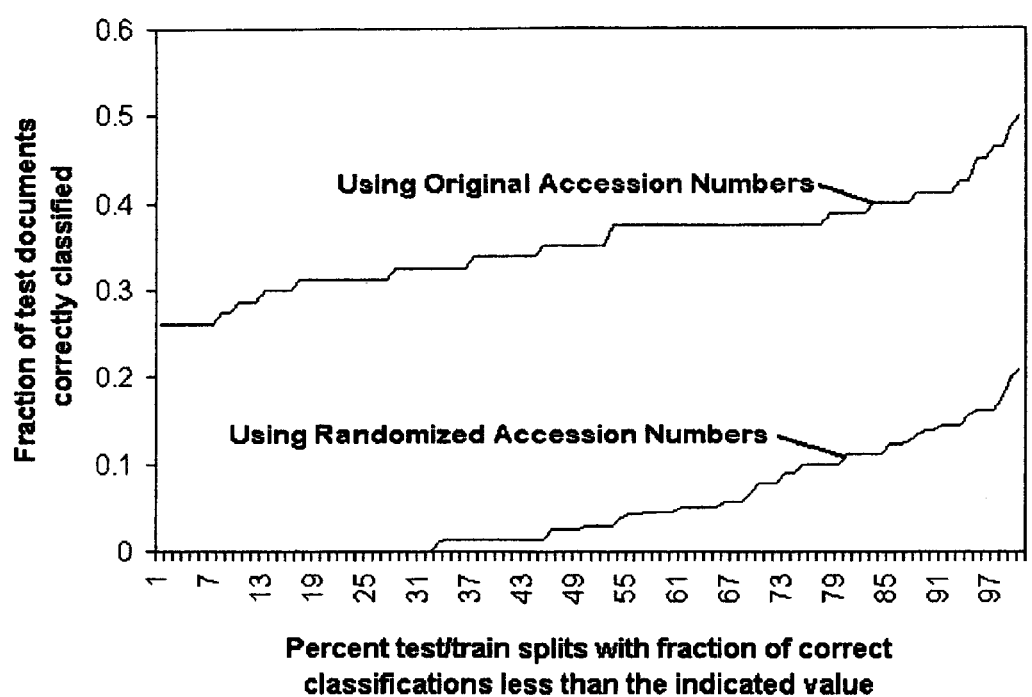
FIG. 3 is a graph showing output from the system and computer program in FIG. 1, providing an example in which the system finds good evidence that a cluster's members are functionally related to one another (Cluster D in IYER et al., supra).
Figure 4:
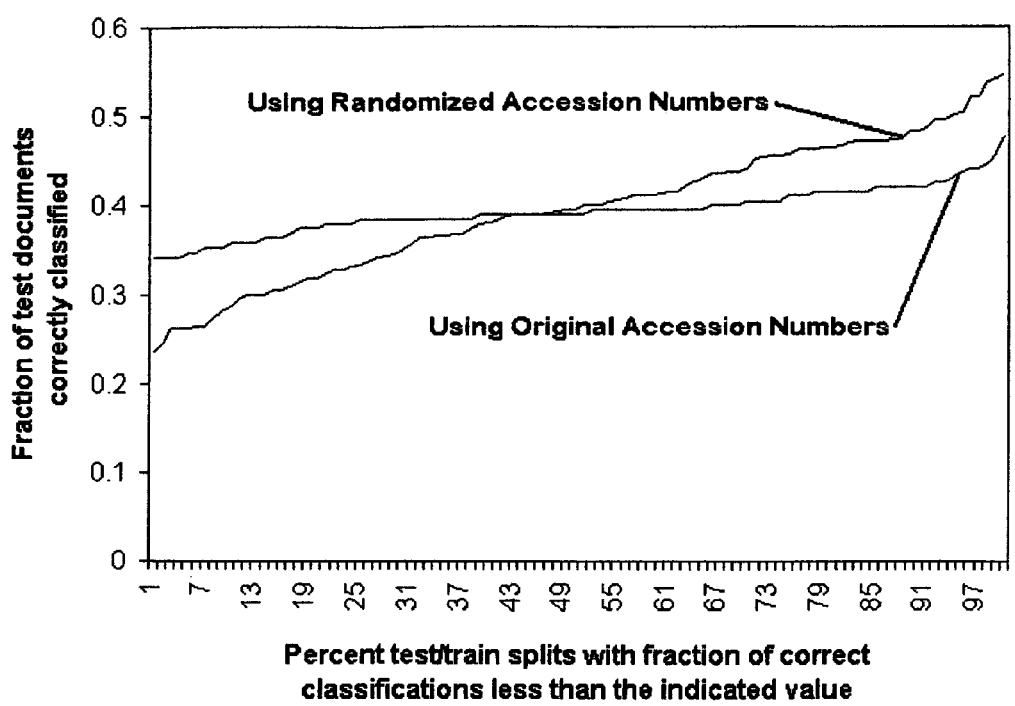
FIG. 4 is a graph showing output from the system and computer program in FIG. 1, providing an example in which the system finds no evidence that a cluster's members are functionally related to one another (Cluster B in IYER et al., supra).

The Text Modeling Module (126) processed the text associated with the accession numbers of the example, as described in the Preferred Embodiment section. The Text Classification, Cluster Randomization, and Data Summarization Program Modules (130, 132, and 134, respectively) then processed the data as described in the Preferred Embodiment. The Data Output Module (136) then presented the results. FIG. 3 and FIG. 4 show representative results when the accession numbers were clustered, as given external to the system in IYER et al., supra.

FIG. 3 shows graphical results for the fourth cluster (Cluster "D") in IYER et al., supra. As described in the Preferred Embodiments section, text about the genes corresponding to accession numbers were randomly split into testing and training sets ("test/train splits"). The default Bayes model was used to model the words in the training set. The model was then used to predict the cluster corresponding to text in the documents in the testing set. The fraction of test documents correctly classified (in FIG. 3, corresponding to Cluster D) was then calculated. The documents in the test/train split were randomized 100 times, so the fraction of correctly classified documents (in FIG. 3, corresponding to Cluster D) was also calculated 100 times. The fractions so obtained were sorted in ascending order, and their values are shown in FIG. 3 (in the graph labeled "Using Original Accession Numbers"). The accession numbers associated with the clusters were also randomized, and the entire process involving test/train splits was repeated 100 times to generate the values also shown in FIG. 3 (in the graph labeled "Using Randomized Accession Numbers"). The graph using the original accession numbers lies significantly above the graph using randomized accession numbers, indicating that the text files corresponding to the original accession numbers for Cluster D are much more predictive of subject matter, than text files corresponding to random accession numbers. The means of these two distributions were calculated by the system, and the difference between the two means (0.302) is taken to be a figure-of-merit for the quality of the cluster. The results shown in FIG. 3 are representative of most of the 10 clusters shown in IYER et al., supra, in the sense that the fraction of correctly classified test documents has a statistical distribution that is consistently larger for the original clustering than for accession numbers randomly assigned to the cluster. The probability that the two distributions in FIG. 3 are the same is less than $10^{-16}$, according to the Kolmogorov-Smirnov test results. The conclusion that may be drawn from this figure is that text about different genes within the cluster uses the same words much more often than text about randomly selected genes. The User may therefore conclude from the results shown in FIG. 3 that the genes represented by this cluster are functionally related, as evidenced by the same words being used in literature about those genes, or that there is independent literature supporting the notion that the similarity of gene expression among genes in this cluster is physiologically meaningful.

FIG. 4 shows graphical results for the another cluster (Cluster "B" in IYER et al., supra). These results are atypical of the clusters in the sense that the fraction of correctly classified test documents has a statistical distribution that is NOT consistently larger for the original clustering than for genes randomly assigned to the cluster. In fact, the difference between the means of the two distributions shown there is only −0.002, a figure of merit that is much worse than the ones for most of the other clusters. The general interpretation of these results is that on average, text about genes within this cluster uses the same words no more often than words found in text about the randomly-selected accession numbers. The User may therefore conclude from the results shown in FIG. 4 that the clustering method used in IYER et al., supra, was unable to find a distinguishing word theme among text about genes in this cluster, or that the literature does not support the notion that the similarity of gene expression among genes in this cluster is physiologically meaningful.

Examples Using the Alternate Embodiments

The example that is described below makes use of the same data that were used in connection with FIGS. 3 and 4, which illustrated the preferred embodiment. As described below, analyzing these data with the alternate embodiment of the method gives results that agree with the analysis using the preferred embodiment.

The example makes use of microarray data that are described in IYER et al. supra, which are available at the Web site having the following domain name—top level domain=edu, second level domain=stanford, third level domain=genome-www. They are from an experiment in which quiescent human diploid fibroblasts were stimulated to proliferate by increasing the concentration of fetal bovine serum in their growth medium. At 12 time points after addition of the serum, samples of mRNA were collected and used to prepare cDNA for hybridizing to an array. Five hundred-seventeen genes on the array were observed to show significant up- or down-regulation, as defined in IYER et al., supra. The microarray data corresponding to these 517 genes were clustered using a hierarchical clustering algorithm [EISEN et al., supra], resulting in 10 clusters, labeled A through J in FIG. 2 of IYER et al., supra. Accession numbers for all the genes represented as spots on the microarray are available at the Web site given above.

Analysis of these data made use of information extracted from Build 96 of the Unigene database, which was contained in the file Hs.data.Z, downloaded from the Web site having the following domain name—top level domain=gov, second level domain=nih, third level domain=nlm, fourth level domain=ncbi fifth level domain=ftp, path=/pub/schuler/Unigene. The analysis also made use of information extracted from the Locus Link database (version Sep. 10, 1999), which was downloaded as the file LL_templ at the Web site having the following domain name—top level domain=gov, second level domain=nih, third level domain=nlm, fourth level domain=ncbi, fifth level domain=ftp, path=/refseq/LocusLink. Processing of these data to associate the accession numbers with Omim numbers proceeded as described in the Preferred Embodiment, through pointers from accession numbers to UniGene numbers to LocusLink numbers to Omim numbers. Among the 517 accession numbers in the test data, 237 of them could be associated with Omim numbers. Most of the others were unidentified ESTs, which were excluded from further analysis by associating them with Omin number "0".

The UID Identification Module (120) in FIG. 2 then downloaded Omim Web pages corresponding to those Omim numbers and extracted from them Unique IDentifier numbers ("uids"), as also described in the Preferred Embodiment. A total of 19,643 uids were associated with 237 Omim numbers, 1944 of which were associated with more than one Omim number.

The Clustering Module (124) in FIG. 2 then clustered the 517 accession numbers using an externally available clustering scheme, which is the one shown in FIG. 2 of IYER et al (1999). The clusters, associated with the accession numbers of the clustered genes, were obtained at the Web site having the following domain name—top level domain=edu, second level domain=stanford, third level domain=genome-www. For use in the example, the clusters that IYER et al (1999) had labeled A through J were relabeled 1 through 10, and accession numbers that had not been associated with a cluster were put into a cluster "zero".

For every possible pair of Omim numbers in each of the subdirectories \0, \1, . . . \Cmax, the Citation Analysis Module (200) went down the list of uid numbers associated with one member of the pair. As it proceeds, it checks to see whether that uid number is also found in the list of uid numbers associated with the other member of the Omim pair. The total number of matches that it found was then divided by the total number of uid numbers associated with one or the other Omim number, whichever of the two have the shorter list. This ratio is defined as the 'coupling strength' between the two Omim numbers.

These coupling strength values, which are associated with each possible pair of Omim numbers (within a subdirectory \0, \1, . . . , or \Cmax) were then stored in the section Coupling Strength Data (202) in the Data Repository (138). When all the coupling strengths were calculated for the pairs of Omim numbers in a subdirectory corresponding to a cluster, these coupling strengths were then averaged to provide an average coupling strength for that cluster, which is also stored in the section Coupling Strength Data (202) in the Data Repository (138).

When all the average coupling strength values had been calculated, the Process Control Module (116) passed control to the Cluster Randomization Module (132). It randomized the assignment of accession numbers to clusters, using the same method that was described in connection with the preferred embodiment. The Process Control Module (116) then passes control back to the Citation Analysis Module (200). The process of calculating an average coupling strength for each of the clusters was then repeated as described above, namely, the association of Omim numbers to the clusters based on their (randomized) accession number composition, the estimation of coupling strength for each pair of Omim numbers in each cluster, and the calculation of an average coupling strength for each cluster. Those results were also stored in the Coupling Strength Data section (202) of the Data Repository (138) for subsequent use. The entire process of accession number randomization and coupling strength calculation is repeated the number of times that was specified as an option by the User (default number of times=100).

The Process Control Module (116) then passed control to the Data Summarization Module (134). For each cluster, the average coupling strengths for the randomized clusters are sorted in ascending order. Then, as an index of the significance of the average coupling strength that had been obtained before randomizing the clusters, the Data Summarization Module (134) determines the percentage of times that the observed coupling strength for each cluster was larger than those obtained with the randomized clusters.

For the data in the example, Cluster D had a percentage coupling score of 82%, suggesting that many genes in this cluster are functionally related. Cluster B, on the other hand, had a percentage coupling strength of only 25%. These results are in agreement with the results shown in FIGS. 3 and 4, which also suggested that the accession numbers (genes) associated with Cluster D are functionally related to one another, whereas the accession numbers (genes) associated with cluster B are not, as judged independently by their associated literature.

CONCLUSION AND SCOPE OF INVENTION

While the above description contains many specifications, these should not be construed as limitations on the scope of the invention, but rather as exemplifications of embodiments thereof.

The invention claimed is:

1. A system for evaluating the quality of gene clustering, comprising:
   (a) means for identifying a set of genes;
   (b) means for partitioning the set of genes in (a) into disjoint subsets of genes known as clusters;
   (c) means for associating documents with each gene in the set of genes in (a), and a means for receiving the text of part or all of each said document;
   (d) means for constructing a compendium of documents for each individual subset of genes known in (b) as a cluster, said compendium consisting of documents containing text that had been received in (c), for all genes that are members of the subset of genes in said cluster;
   (e) means for dividing each and every compendium of documents in (d) into two parts, a training compendium of documents and a testing compendium of documents;
   (f) means for using words or phrases in the text of all the training compendia in (e) to train a document classifier, said training being performed by the computer program Rainbow using any of the classification algorithms that said program implements;
   (g) means for using words or phrases in the text of each document in each testing compendium in (e), to test the document classifier trained in (f), wherein the classifier predicts the cluster with which each test document is associated;
   (h) means for calculating and storing the number of documents in the test compendia in (e) that are correctly and incorrectly predicted to be associated with each cluster, upon testing with the trained document classifier as provided in (g);
   (i) means for repeatedly and randomly dividing documents into different training and test compendia as provided in (e), for using each such division to calculate a fraction of correct classifications for each cluster as provided in (f)-(h), and for storing said fractions for each and every such random division of documents into different training and test compendia;
   (j) means for repeatedly and randomly partitioning the set of genes in (a) into subsets, wherein the sizes of the random subsets of genes are matched to sizes of the clusters provided in (b); for re-associating a set of documents and text with each gene in the set as provided in (c); for making available means (d)-(h) so as to be able to calculate a fraction of correct classifications for each of the random gene partitions that are matched to the clusters provided in (b); and for storing said fractions for each and every such random partitioning of the set of genes in (a);
   (k) means for calculating the distribution of fractions of correctly classified documents that were generated by repeated, random partitioning of documents as provided in (i), and for the distribution of fractions of correctly classified documents that were generated by repeated, random partitioning of the set of genes as provided in (j); and for calculating a figure-of-merit for each cluster so as to characterize the difference between said distributions for each cluster;
   (l) means for displaying the distributions and their corresponding figure-of-merit as provided in (k), for each cluster as provided in (b), as an output to a user of the system;
   whereby said figure-of-merit for each cluster provides to a user of the system an indication of the extent to which some words and phrases, present in documents associated with genes in said cluster, collectively distinguish that cluster from all the other clusters, and whereby said figure-of-merit for each cluster provides to a user of the system an indication of the quality of that cluster.

2. A system for evaluating the quality of gene clustering, comprising:
   (a) means for identifying a set of genes;
   (b) means for partitioning the set of genes in (a) into disjoint subsets of genes known as clusters;
   (c) means for associating a set of literature documents with each gene in the set of genes in (a);
   (d) means for calculating for every pair of genes within a cluster in (b) a coupling strength index, said index being proportional to the number of times that any document in (c) is associated with both members of said pair of genes; and for storing said set of index values for every cluster;
   (e) means for repeatedly and randomly partitioning the set of genes in (a) into subsets, wherein the sizes of the random subsets are matched to the sizes of the clusters provided in (b); for re-associating a set of documents with each gene in the set as in (c); for making available means (d) so as to calculate coupling strength indices; and for storing said set of index values for every such random subset;
   (f) means for calculating for every cluster in (b) and random subset in (e) a measure of central tendency for the set of coupling strength index values that are stored as provided in (d) and (e);
   (g) means for calculating for every cluster in (b) the percentage of times that the central tendency calculated in (f) is larger than the corresponding central tendency among those calculated repeatedly for corresponding random subsets in (e);
   (h) means for displaying the percentage calculated in (g), for each cluster in (b), as an output to a user of the system;
   whereby said percentage for each cluster provides to a user of the system an indication of the extent to which documents associated with genes in said cluster collectively distinguish that cluster from all the other clusters, and whereby said percentage for each cluster provides to a user of the system an indication of the quality of that cluster.

* * * * *